United States Patent [19]
Jönsson et al.

[11] Patent Number: 5,344,231
[45] Date of Patent: Sep. 6, 1994

[54] SYSTEM FOR THE PREPARATION OF A FLUID CONCENTRATE INTENDED FOR MEDICAL USE

[75] Inventors: Lennart Jönsson, Furulund; Stefan Knutsson, Bjärred, both of Sweden

[73] Assignee: Gambro AB, Sweden

[21] Appl. No.: 3,844

[22] Filed: Jan. 11, 1993

Related U.S. Application Data

[63] Continuation of Ser. No. 643,468, Jan. 22, 1991, abandoned.

[30] Foreign Application Priority Data

Feb. 19, 1990 [SE] Sweden .................. 9000586-9

[51] Int. Cl.⁵ ............................................ B01F 15/04
[52] U.S. Cl. ................................. 366/137; 366/152; 366/160; 222/145
[58] Field of Search ............... 366/137, 136, 144, 146, 366/150, 151, 152, 153, 154, 155, 159, 160; 137/268; 222/52, 145, 325; 422/68.1, 278, 281; 604/81, 82, 84

[56] References Cited

U.S. PATENT DOCUMENTS

| | | | |
|---|---|---|---|
| 2,152,956 | 4/1939 | Etzkorn | 366/177 |
| 2,365,293 | 12/1944 | Robinson | 366/136 |
| 3,653,640 | 4/1972 | De Haas | 366/151 |
| 4,158,034 | 6/1979 | Riede | 210/321.69 |
| 4,385,840 | 5/1983 | Wisneski | 222/145 |
| 4,474,310 | 10/1984 | Muller | 222/145 |
| 4,764,019 | 8/1988 | Kaminski | 366/136 |
| 4,784,495 | 11/1988 | Jonsson | 366/160 |
| 4,823,987 | 4/1989 | Switall | 366/153 |
| 4,844,620 | 7/1989 | Lissant | 366/136 |
| 5,076,702 | 12/1991 | Smals | 366/160 |

FOREIGN PATENT DOCUMENTS

| | | | |
|---|---|---|---|
| 1034464 | 1/1954 | Fed. Rep. of Germany . | |
| 1034464 | 7/1958 | Fed. Rep. of Germany | 366/136 |
| 0085187 | 3/1990 | Japan | 222/145 |
| 78191 | 6/1955 | Netherlands | 366/136 |
| 0806086 | 2/1981 | U.S.S.R. | 366/136 |

*Primary Examiner*—Timothy F. Simone
*Assistant Examiner*—Randall E. Chin
*Attorney, Agent, or Firm*—Lerner, David, Littenberg, Krumholz & Mentlik

[57] ABSTRACT

Apparatus for the preparation of fluids intended for medical use is disclosed, including a source of pure water and at least one cartridge or other vessel containing a powder which is to be dissolved in the water for preparation of the desired fluid. The apparatus includes a container such that the water and a powder or powder concentrate can be mixed and a concentrate provided in the container, and a recirculation circuit for recirculation of the water or concentrate solution into the container for further mixing of the water and powder or powder concentrate to prepare a concentrate having a predetermined concentration.

25 Claims, 5 Drawing Sheets

SYSTEM FOR THE PREPARATION OF A FLUID CONCENTRATE INTENDED FOR MEDICAL USE

This is a continuation of application Ser. No. 07/643,468 filed Jan. 22, 1991, now abandoned.

FIELD OF THE INVENTION

The present invention relates to systems for the preparation of fluids and fluid concentrates which are intended for medical use. More particularly, the present invention relates to systems for the preparation of concentrate solutions intended for medical uses, such as dialysis fluid, replacement fluids for hemofiltration, and concentrates for the preparation of such fluids. More particularly, the present invention relates to such systems which include a source of pure water and at least one cartridge or other such vessel containing a powder or powder concentrate which is intended to be dissolved in the water for the preparation of the desired fluid.

BACKGROUND OF THE INVENTION

Previous systems for the preparation of such fluids normally operate beginning with one or more liquid based concentrates. For example, U.S. Pat. No. 4,158,034 describes how a concentrate in liquid form is mixed with water for the preparation of a dialysis fluid. In European Patent No. EP-B1-0 22 922, and in U.S. Pat. No. 4,783,273, there is a description of how two liquid-based concentrates can be mixed with water to obtain a fluid intended for medical use, such as a a dialysis fluid. More recently, systems have been introduced which instead make use of one or more concentrates in powder form. For example, U.S. Pat. No. 4,784,495 describes how one or more such powder-based concentrates can be used, with or without the addition of a liquid-based concentrate.

Should one wish to utilize a powder-based concentrate which is difficult to dissolve, it can become quite difficult to achieve acceptably rapid dissolution such as by using the system disclosed in the above-mentioned U.S. Pat. No. 4,784,495. Furthermore, the system according to this patent can become relatively complicated if it is desired to add several different individual pre-packed powder-based concentrates.

SUMMARY OF THE INVENTION

In accordance with the present invention, these are the problems that have now been solved by the discovery of apparatus for the preparation of a concentrate solution from water and powder or powder concentrate comprising water supply means for supplying water, mixing means comprising a container whereby the water supply means can supply the water to the container and the powder or powder concentrate can be mixed with the water in the container to provide the concentrate solution, withdrawal means for withdrawing the concentrate solution from the container, and recirculation means for recirculating the concentrate solution into the container for further mixing of the water with the powder or powder concentrate to further concentrate the concentrate solution to a predetermined concentrate. It will therefore be appreciated that the term mixing means as used in the present application can also be expressed as dissolution means for dissolving the powder or powder concentrate in water. In accordance with this invention, this apparatus can thus be used for the preparation of fluids intended for medical use, such as dialysis fluid, replacement fluid for hemofiltration, or a concentrate for the preparation of such fluids.

In accordance with a preferred embodiment of the apparatus of the present invention, the recirculation means thus includes cartridge means whereby during recirculation the water or concentrate solution passes through the cartridge means so that powder or powder concentrate contained within the cartridge means can be mixed with the water or the recirculating concentrate solution to provide the concentrate solution and to further concentrate the concentration solution.

In accordance with the present invention, a system is thus provided which includes means for conducting water to a mixing vessel and which includes a recirculation circuit which includes the mixing vessel as well as one or more cartridges or means for connecting one or more cartridges thereto, and means for recirculation of the water or partially prepared concentrate solution through one or more of the cartridges until an appropriate concentration is obtained by dissolving the powder either partially or fully into the solution. By use of such a recirculation circuit, even relatively difficult to dissolve powder-based concentrates can now be dissolved appropriately, and at the same time liquid-based concentrates can be prepared in the mixing vessel from one or more powder-based concentrates which, after preparation, can be conveyed to conventional dialysis machines which would otherwise normally receive such liquid-based concentrates from one or more containers therefor.

In accordance with a preferred embodiment of the apparatus of the present invention, the recirculation means includes a plurality of cartridge members and flow control means for controlling the flow of the recirculation means whereby the water or concentrate solution circulating in the recirculation means can be selectively directed to one of the plurality of cartridge members to mix powder or powder concentrate contained within that one of the cartridge members with the water or concentrate solution. These plurality of cartridges are thus connected in parallel for such selective connection to the recirculation circuit. In this manner, the precise desired amount of concentrate for the patient can be removed from each cartridge; i.e., an individual dosage can be obtained therefrom.

Furthermore, since not all substances are suitable for use in a powdered form, one or more of the cartridges connected in such a parallel arrangement can constitute a vessel for a liquid-based concentrate which is intended to be included in the finally prepared concentrate fluid therefor.

In accordance with a preferred embodiment of the apparatus of the present invention, the pump means comprises a metering pump for metering the water or concentrate solution provided by the mixing means.

In accordance with another embodiment of the apparatus of the present invention, the recirculation means includes concentration determination means which may include conductivity measuring means for measuring the conductivity of the concentrate solution, whereby the recirculation of the concentrate solution in the recirculation means can be controlled thereby. In this manner, the recirculation through the particular cartridge can be terminated when the desired conductivity is obtained. Suitable such means for measuring the concentration, such as pH meters or ion-selective meters, can also be used for this purpose. Indeed, when conductivity meters are referred to throughout this specification, this same type of substitution can be made therefor.

In accordance with a preferred embodiment of the apparatus of the present invention, when a plurality of cartridges in parallel are employed in the recirculation means, the flow through these cartridges can be controlled by a valve unit, which is arranged to selectively connect the cartridge and/or vessel to the recirculation circuit.

In accordance with another embodiment of the apparatus of the present invention, there is also provided secondary cartridge means, and the water supply means includes secondary water conduit means for conducting the water to the secondary water cartridge means, whereby additional powder or powder concentrate contained within the secondary cartridge means can be mixed with the water and a secondary concentrate solution produced therein, and secondary mixing means for mixing the secondary concentrate solution with the concentrate solution withdrawn from the recirculation means by the withdrawal means so as to provide a combined concentrate solution. In this manner, not all of the cartridges need to be included in the recirculation circuit and, instead, the water can be also conducted directly to a cartridge which is connected in parallel to the other cartridges for dissolving the substance therein which is intended to form part of the finally prepared concentrate solution.

In a preferred embodiment, a conductivity measuring means for measuring the conductivity of the secondary concentrate solution is provided, or conductivity measuring means for measuring the conductivity of the combined concentrate solution, or conductivity measuring means for measuring both conductivities. Furthermore, if such conductivity measurements are made both before and after mixture of these two solutions, then a differential conductivity means may be utilized. This is particularly suitable where only a small change in conductivity occurs due to the mixing of these two solutions.

In accordance with another embodiment of the apparatus of the present invention, in the case where conductivity measuring means for measuring the conductivity of the combined concentration solution is employed, the recirculation means preferably includes metering pump means for controlling the flow of the combined concentrate solution. The use of an accurate metering dosage pump theoretically permits one to calculate which portion of the conductivity is due to the concentrate solution and which portion is due to the dissolved concentrate in the secondary concentrate solution.

In accordance with another embodiment of the apparatus of the present invention, closure valve means are provided in connection with the water supply means, whereby the supply of water can be terminated when the mixing means contains a predetermined quantity of water. The mixing vessel can, for example, include a level indicator which, in turn, controls the closure valve means arranged in the water supply means.

In accordance with another embodiment of the apparatus of the present invention, cartridge means are associated with the water supply means whereby powder or powder concentrate contained within the cartridge means can be mixed with the water and supplied to the mixing means therefrom. This embodiment is particularly useful when liquid-based or very readily dissolvable powder concentrates are to be supplied to the mixing means.

In accordance with this invention, the cartridges and/or vessels discussed above can initially contain an excess of powder concentrate, such that circulation in the recirculation circuit can be interrupted before the cartridge or other vessel connected to the recirculation circuit is totally empty. In this manner, it is assured that the desired concentration of the added substance can always be obtained.

In accordance with a preferred embodiment of the apparatus of the present invention, the apparatus includes tertiary cartridge means and the water supply means includes tertiary water conduit means for conducting the water to the tertiary cartridge means, whereby additional powder or powder concentrate contained within the tertiary cartridge means can be mixed with the water and a tertiary concentrate solution produced therein, and tertiary mixing means for mixing the tertiary concentrate solution with at least one of the concentrate solutions drawn from the recirculation means by said withdrawal means and said secondary concentrate solution. Preferably, the apparatus also includes conductivity measuring means for measuring the conductivity of the tertiary concentrate solution, and/or conductivity measuring means for measuring the conductivity of the one of the combined concentrate solutions and the secondary concentrate solution.

In accordance with one embodiment of the apparatus of the present invention, the mixing means comprises a cartridge or other vessel which contains the desired quantity of a salt from the outset. In this manner, this salt can also be readily dissolved in the recirculation circuit thereof, and when fully dissolved this can be checked by means of a conductivity meter, for example. Particular advantages can also be obtained if the mixing vessel contains a small quantity of liquid, preferably water, in addition to that salt in a manner such that a concentrated liquid or mud of that liquid and the powder-based salt is formed therein. Such a concentrated liquid can be more readily checked to see that it is lump-free compared with a generally compacted powder in dry form.

In accordance with another embodiment of the apparatus of the present invention, heating means are included in the recirculation means for heating the concentrate solutions recirculating in the recirculation means. This permits the salt in the form of a dry powder or concentrated liquid to be more readily dissolved.

In accordance with another embodiment of the apparatus of the present invention, the apparatus includes acid supply means for supplying acid to the recirculation means. Preferably, the acid supply means includes acid storage means for storing the acid and acid pump means for pumping the acid from the acid storage means to the recirculation means. This embodiment particularly applies to the case where the mixing vessel contains a concentrated liquid aside from the salt. Many medical solutions, such as dialysis fluids, should actually contain such an acid, and in this case it can be added before preparation of the final solution. As an alternative, the acid can be added by means of the recirculation circuit being connected to a branch circuit with a dosage pump arranged to pump an acid in liquid form from a storage vessel to the recirculation circuit.

In accordance with another embodiment of the apparatus of the present invention, the recirculation means includes sterile filter means for filtering the concentrate solution before the concentrate solution enters the mixing means.

In accordance with another embodiment of the apparatus of the present invention, the recirculation means includes quick release connection means connecting the mixing means to the recirculation means, whereby the mixing means can be readily uncoupled from the recirculation means. In this manner, the mixing vessel can then be easily coupled to, for example, a dialysis machine instead of the traditionally employed dialysis concentrate container.

In accordance with a preferred embodiment of the apparatus of the present invention, the mixing means comprises a flexible plastic bag. By using such a bag, it can be readily observed whether the salt is lump-free whether it is in dry form or in the form of a liquid concentrate, or in the form of a salt slurry.

DETAILED DESCRIPTION

Figure 1:
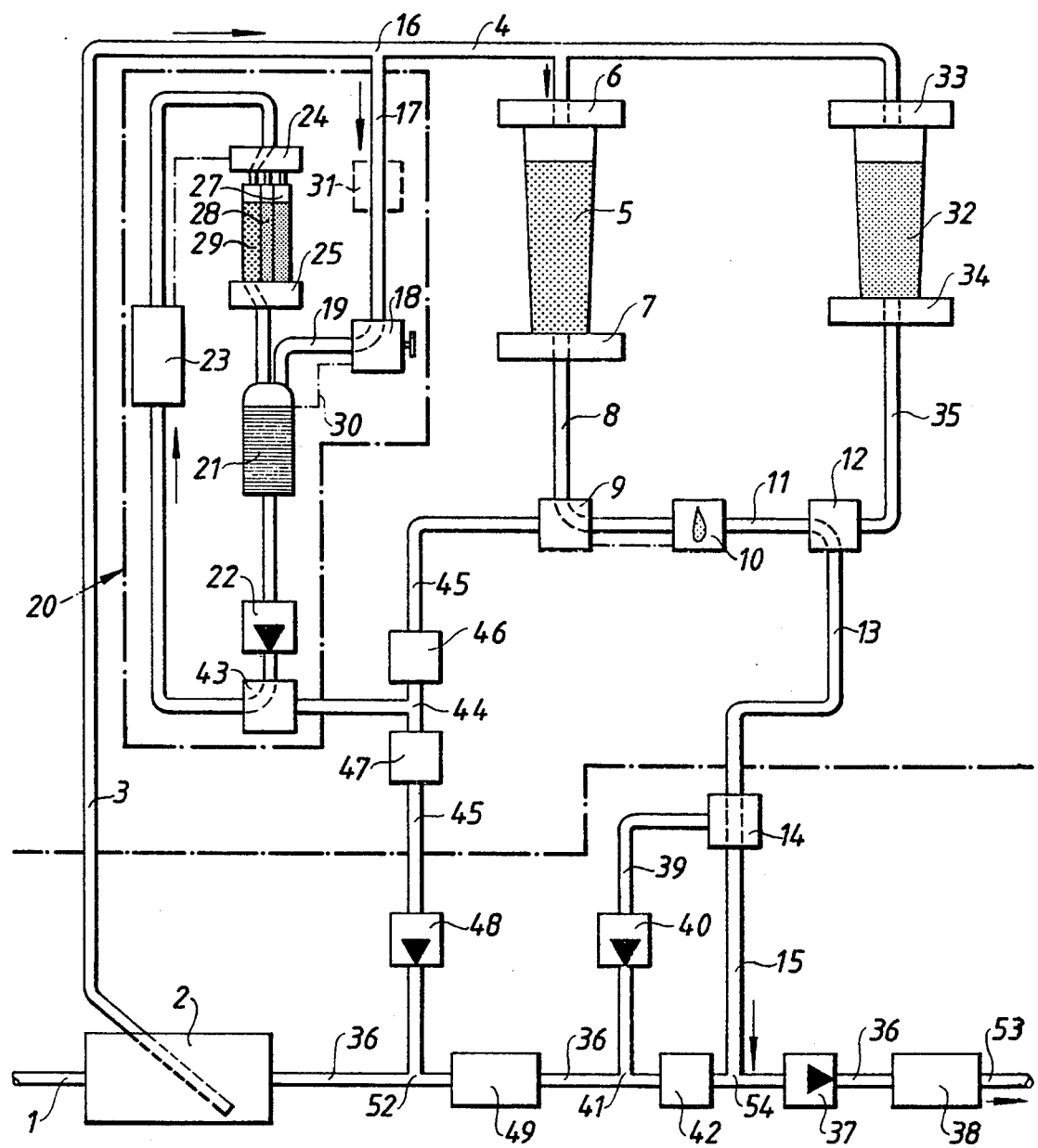
FIG. 1 is a schematic representation of a preferred embodiment of the system in accordance with the present invention.
Figure 2:
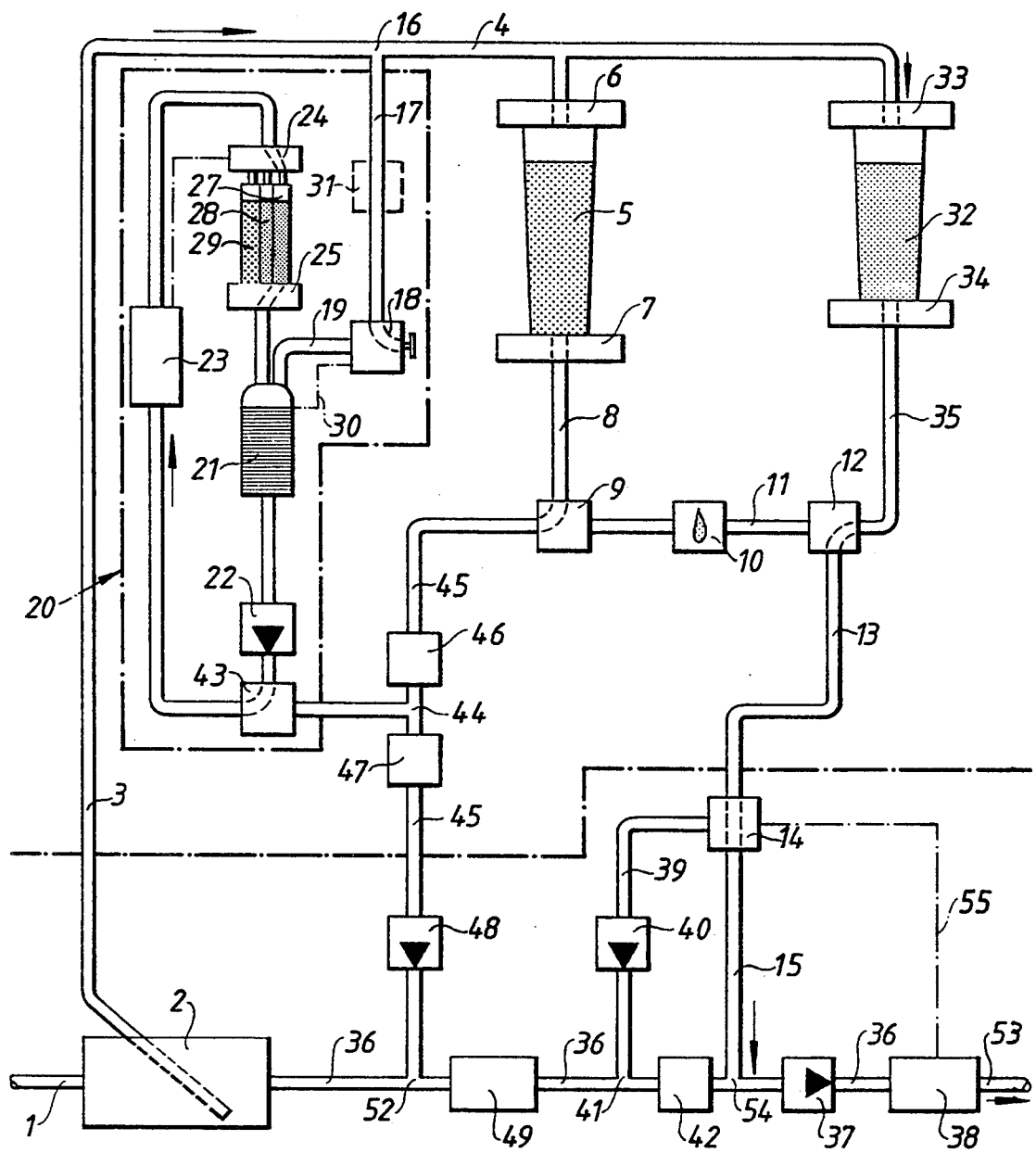
FIG. 2 is a schematic representation of the system shown in FIG. 1 in an altered form.
Figure 3:
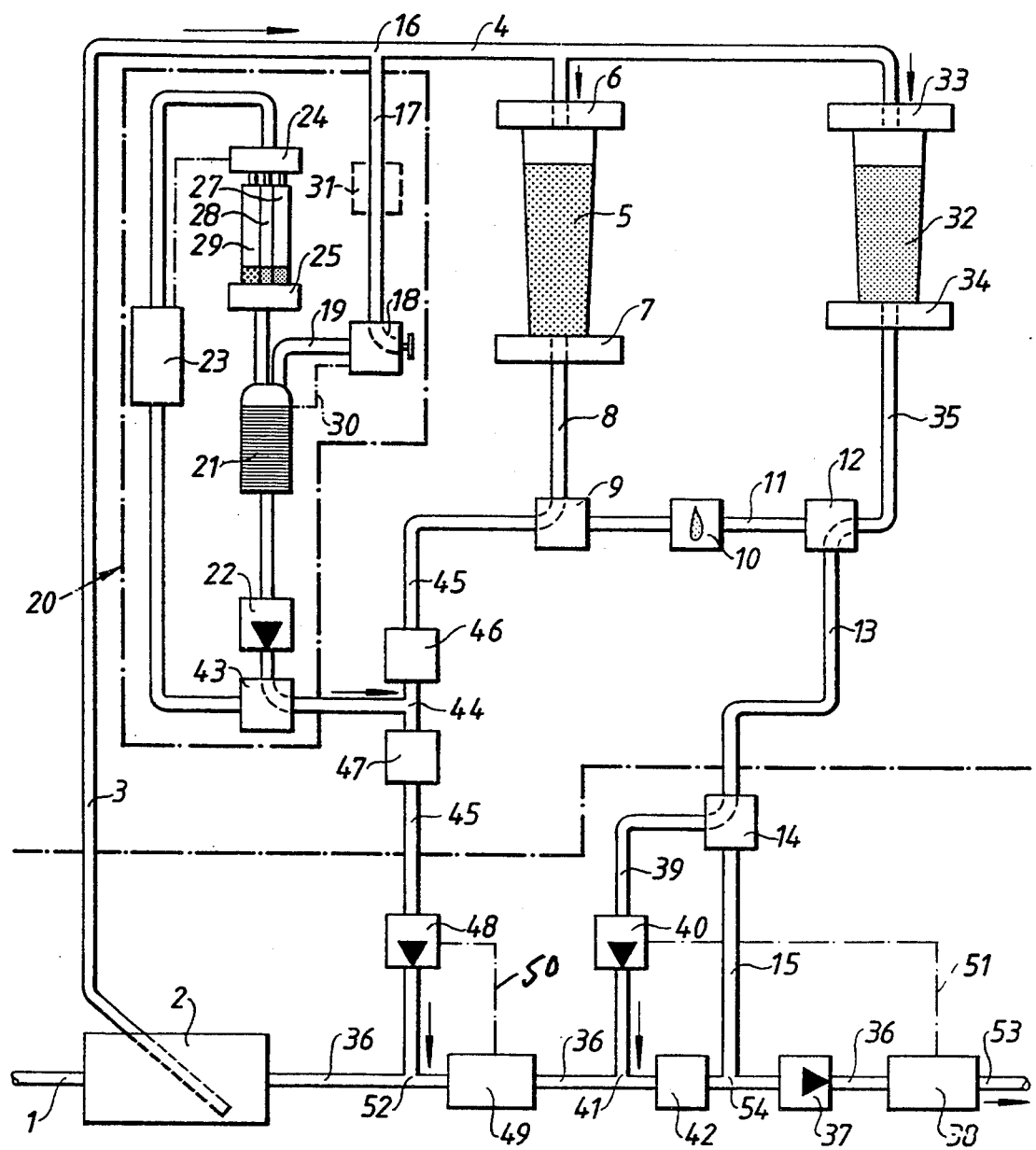
FIG. 3 is a schematic representation of the system shown in FIG. 1 in a further altered form.

Referring to the Figures, in which like reference numerals refer to like portions thereof, FIGS. 1-3 show by way of a block diagram a preferred embodiment of the system according to the present invention in its three different configurations. FIG. 1 is intended to show how a recirculation circuit 20, and a separate powder cartridge 5 are, respectively, filled with water. The water is taken from an inlet 1, through a heating vessel 2, and through conduits 3 and 4 to powder cartridge 5, which is located between two connection pieces 6 and 7. When the cartridge 5 is filled, the water is further passed as shown in FIG. 1 through a conduit 8 and a valve 9 to a detector 10, which detects the water and/or concentrate dissolved therein. It is possible to carry this out with a time delay so that the fluid will have time to fill conduit 11, valve 12, conduit 13, valve 14, and conduit 15.

At the same time, water is conveyed from a branch point 16 through conduit 17, valve 18 and conduit 19, to a recirculation circuit, which in its entirety is denoted by reference numeral 20. Recirculation circuit 20 includes a mixing vessel 21, a recirculation pump 22, a concentration measuring device 23, such as a conductivity meter, and between two valve units 24 and 25, there are connected in parallel a number of cartridges or other vessels 27, 28 and 29 for one or more powder concentrates or liquid-based concentrate. When a sufficient quantity of fluid has been supplied to the mixing vessel 21, valve 18 is closed. This can occur with the assistance of a level indicator, which is schematically shown in FIG. 1 by the dashed line 30. Thereafter, the recirculation pump 22 is initiated, along with valve units 24 and 25, which are so positioned that the water is passed through one of the vessels or cartridges 27-29. In FIG. 1 it is vessel 29 which is shown as being thus connected. When the desired conductivity is obtained, which is measured by means of meter 23, the next cartridge 28 can then be connected, and finally cartridge 27. Should the prepared fluid in mixing vessel 21 include another liquid-based or easily dissolvable concentrate, then dissolution can occur during the filling of mixing vessel 21, with the vessel containing this concentrate being connected to conduit 17. Such a vessel 31 is shown in FIG. 1 by means of dashed lines.

When the recirculation circuit 20 is filled, valve 18 is closed, as shown in FIG. 2. In the same manner, valve 9 is actuated when vessel 5 is filled. This valve position is also shown in FIG. 2. At the same time, valve 12 is switched from the position shown in FIG. 1 to that shown in FIG. 2, so that water from conduit 4 can pass to another vessel or powder cartridge 32, which is located between two connection pieces 33 and 34. When cartridge 32 has been filled, the water with dissolved concentrate therein Can be conducted through conduit 35, valve 12, conduit 13, valve 14 and conduit 15 to a main line or conduit 36, which includes a pump 37 and a detector 38, such as a conductivity measuring device. Detector 38 controls valve 14, so that it is then switched to the position shown in FIG. 3. The fluid from vessel 32 is now conveyed from valve 14 through a conduit 39, which includes a dosage pump 40, to the main line 36 at a point 41 upstream of a restrictor 42. This restrictor 42, together with pump 37 and a gas trap, arranged further downstream (not shown in FIG. 3), is used for degasing the prepared fluid.

By switching valve 14 to the position shown in FIG. 3, the system is ready to provide a solution for use in dialysis. An inlet valve 43 in the recirculation circuit 20 is thus actuated so the pump 22 can pump prepared fluid from the mixing vessel 21 to a mixing point 44, to which concentrate from the vessel 5 is conducted by means of valve 9 and conduit 45. The appropriate concentration of the dissolved substance is measured in this conduit upstream and downstream of the mixing point 44. This can be achieved, for example, by means of a differential conductivity meter, whose measuring points are denoted by reference numerals 46 and 47, respectively. The prepared solution can then be conducted further through conduit 45 by means of pump 48, which preferably consists of an accurately metering dosage pump. The prepared solution can thus be conducted to the main line 36, in which the concentration is once more checked by means of a meter 49, such as another conductivity measuring device. This meter 49 then controls pump 48, as shown by the dotted line 50 in FIG. 3. Additional concentrate is then added to the prepared solution at mixing point 41 by means of a pump 40, which is controlled by measuring device 38, as indicated by the dotted line 51. By means of measuring device 38, which preferably consists of a conductivity meter, it is possible to regulate the final concentration of the concentrate solution obtained from the system according to this invention.

Figure 4:
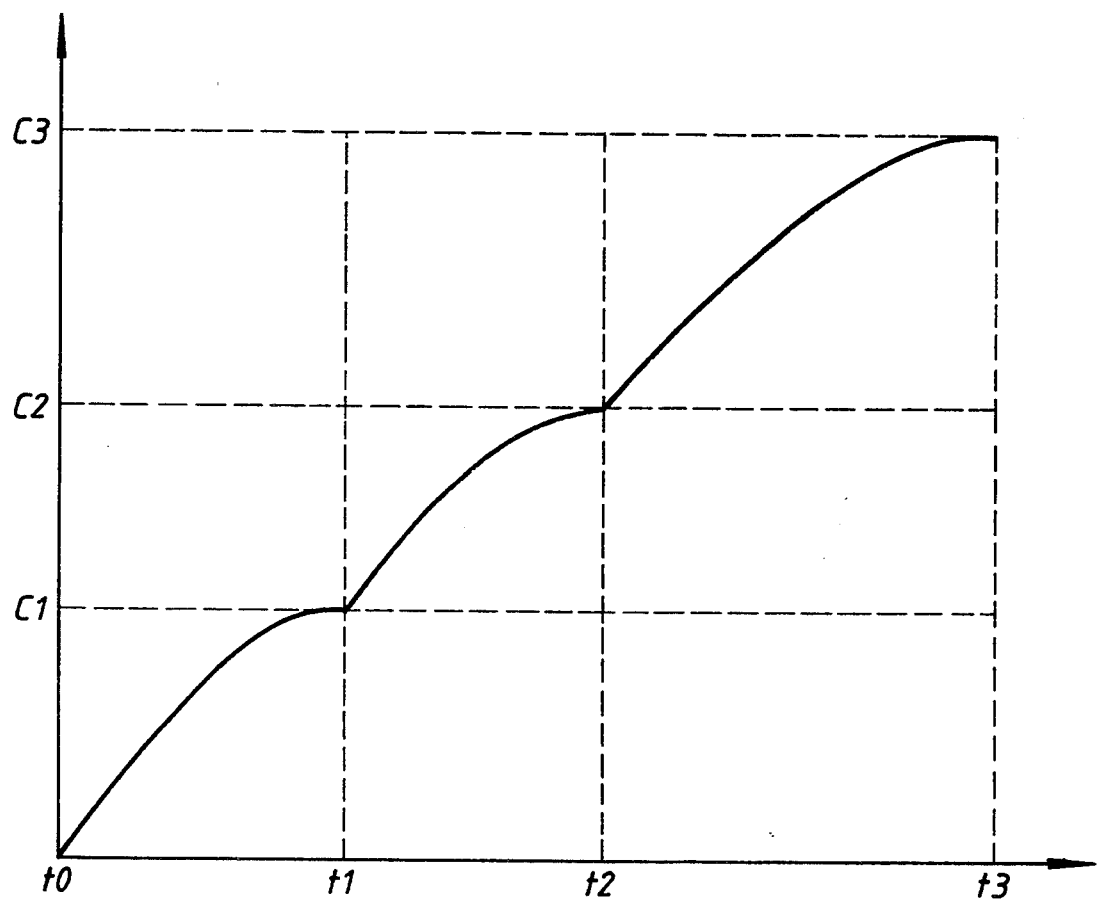
FIG. 4 is a graphical representation measuring conductivity versus time using the supply of three different concentrates in accordance with the system shown in FIGS. 1-3.

Referring next to FIG. 4, there is shown a diagram of how the conductivity varies in recirculation circuit 20. It is assumed in this case that meter 23 consists of a conductivity measuring device, and that vessels 27, 28 and 29 contain three different salts. Thus, between time t0 and t1 one of these vessels is connected, until conductivity value c1 is obtained. Thereafter, the next vessel is connected until conductivity value c2 is reached. Then the third or final vessel is connected until the conductivity obtains the desired value c3. At this point, valve 43 is switched over so that the thus-prepared solution can be conducted to mixing point 44. At this mixing point, concentrate from vessel 5 is added. The mixture thus obtained is then fed to mixing point 52 in main line 36, where it is mixed with water from heating vessel 2. At the next mixing point 41, concentrate from vessel 32 is then added. After a final check in the measuring device 38, the thus-prepared solution can then be conducted to its place of consumption, as symbolized by arrow 53.

Figure 5A:
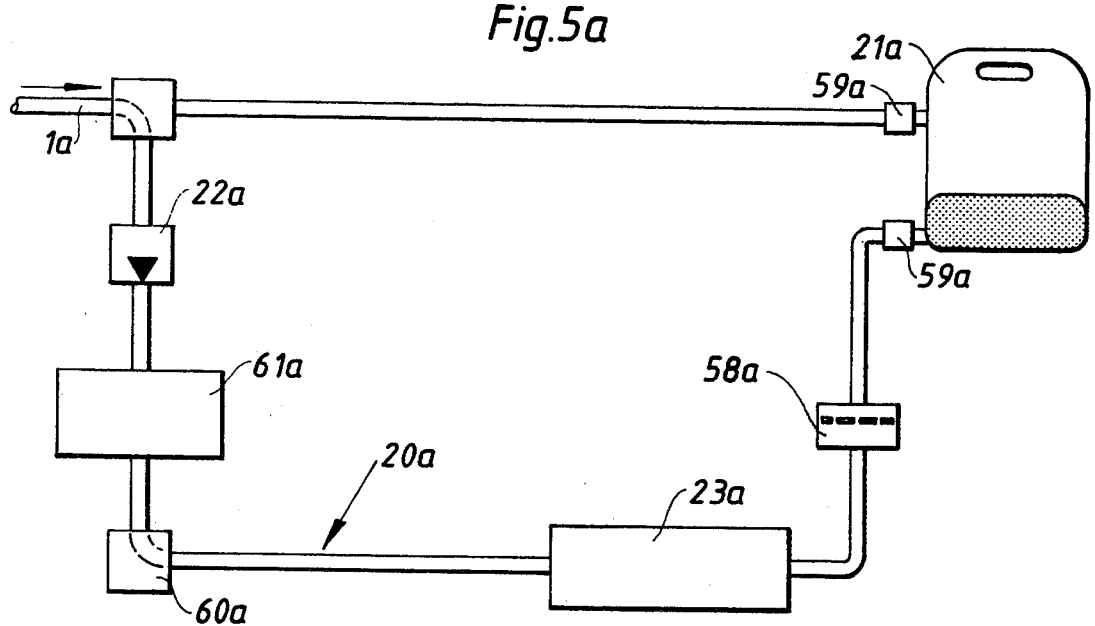
FIG. 5a is a schematic representation of a modified embodiment of the system in accordance with the present invention.
Figure 5B:
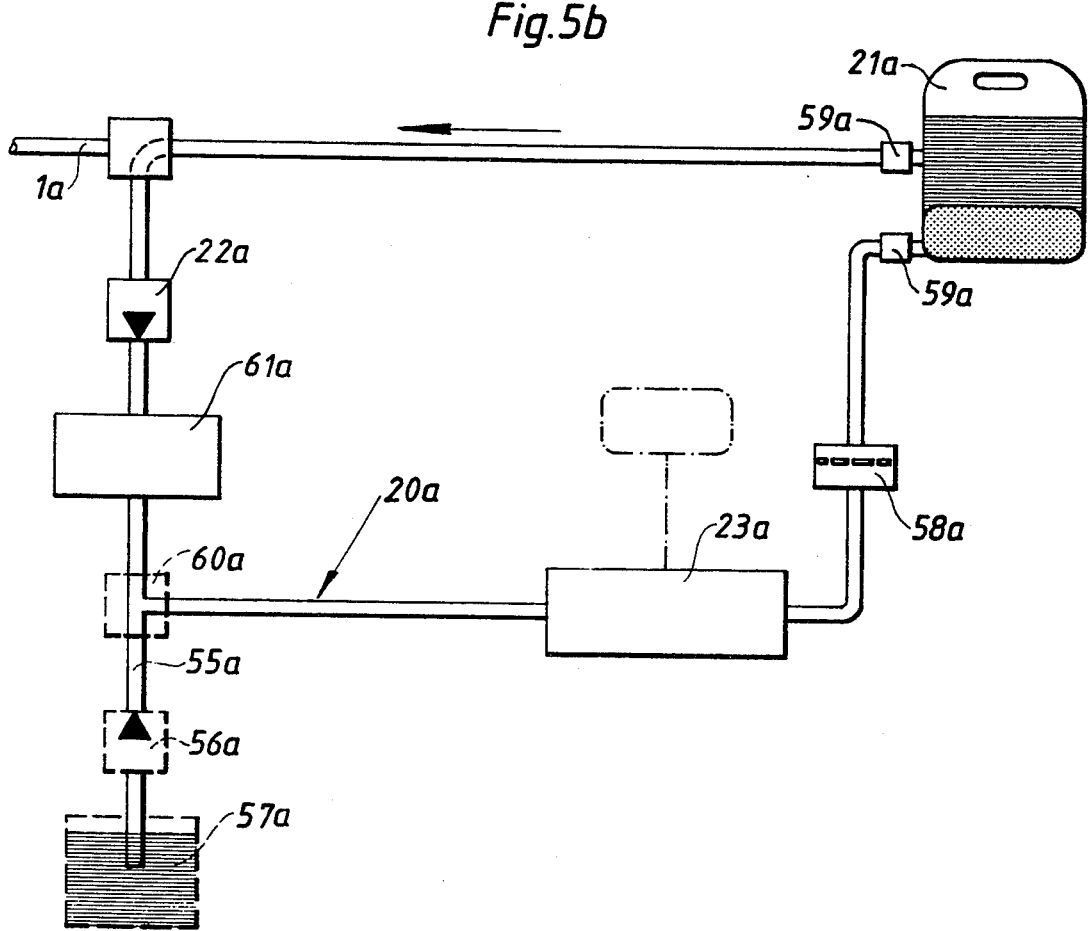
FIG. 5b shown a schematic representation of a further modified embodiment of the system in accordance with the present invention.

Finally, FIGS. 5a and 5b show a modification of the system according to the present invention. Since this modification still corresponds in principal to the above-described system, the same reference numerals have been used, but with the addition of a. In this system, pure water enters through inlet 1a and is pumped by means of pump 22a through recirculation circuit 20a, which includes a heater 61a, a control device, such as a conductivity meter 23a, a sterile filter 58a and a mixing vessel 21a. Utilizing this arrangement, mixing vessel 21a should contain the desired quantity of salt from the outset. This salt can possibly be in a dry form, or it can be a concentrated liquid obtained by adding a small quantity of liquid thereto. Such a concentrated liquid can be complemented by the addition of any necessary acid in liquid form. Such acid may, however, also be added in different forms. Certain acids can, for example, be obtained in the form of a dry powder.

Acid in liquid form can be added through a branch conduit 55a with a dosage pump 56a, as is shown in FIG. 5b. The acid can thus be drawn from a vessel 57a, and introduced into the recirculation circuit by means of valve 60a. The mixing vessel 21a is preferably connected to the recirculation circuit 20a by means of quick-release connectors 59a, so that it can be readily uncoupled and connected, for example, to a dialysis machine, instead of the traditionally employed dialysis concentrate container.

EXAMPLE 1

Utilizing the system described in FIGS. 5a and 5b for preparation of a dialysis liquid solution, the following mixture was present in vessel 21a:

NaCl≃1,050 grams

Kcl≃13 grams

Cacl≃45 grams

MgCl≃18 grams

All of these salts were present in the form of a powder. To this was added approximately 2 dl of fluid, essentially comprising water, but to which approximately 32 g of acetic acid had been added. In this case a flexible plastic bag was used for the mixing vessel 21a. In this manner, it was possible to check that a lump-free concentrated liquid was obtained. It should be appreciated, however, that a somewhat smaller quantity of liquid can be used. Alternatively, an excess of liquid can be added, but for practical reasons it is advisable to keep the weight of the mixing vessel 21a and its contents down.

Naturally the invention is not limited simply to the embodiment described above, but may be varied within the scope of the following claims. The parts included in the system may thus be varied within wide limits with regard to their form as well as their function. For example, the containers 27–29 and 31 can be combined together, such as in the form of a flexible bag or the like, with a desired number of compartments therein.

We claim:

1. Apparatus for the preparation of a concentrate solution from water and powder or powder concentrate comprising water supply means for supplying said water, dissolution means for dissolving said powder or powder concentrate in said water, said dissolution means comprising a container whereby said water supply means is adapted to supply said water to said container and at least a portion of said powder or powder concentrate can be dissolved in said water so as to provide said concentrate solution in said container, withdrawal means for withdrawing said concentrate solution comprising a mixture of said water and said powder concentrate from said container, and recirculation means for recirculating said concentrate solution into said container for further dissolution of said water with said powder or powder concentrate to further concentrate said concentrate solution to a predetermined concentration, said recirculation means including at least one conduit for providing a recirculation path for said concentrate solution during said recirculation, a plurality of cartridge members selectively connected to said at least one conduit, at least one of said plurality of cartridge members containing said powder or powder concentrate, and flow control means for controlling the flow in said recirculation means, said flow control means including concentration determination means for determining the concentration of said concentrate solution and regulating the concentration thereof, and valve means connected to said at least one conduit, said valve means being operatively associated with said concentration determination means for selectively providing a flowpath for said concentrate solution recirculating in said recirculation means to one of said plurality of cartridge members in response to said concentration determination means whereby said powder or powder concentrate contained within said one of said cartridge members is further dissolved in said concentrate solution.

2. The apparatus of claim 1 wherein said flow control means further comprises pump means connected to said at least one conduit for facilitating said recirculation of said concentrate solution in said recirculation means.

3. The apparatus of claim 2 wherein said pump means comprises metering pump means for metering said water or concentrate solution provided by said dissolution means.

4. The apparatus of claim 1 wherein said concentration determination means includes conductivity measuring means for measuring the conductivity of said concentrate solution whereby the recirculation of said concentrate solution in said recirculation means can be controlled thereby.

5. The apparatus of claim 1 including secondary cartridge means having additional powder or powder concentrate therein, and wherein said water supply means includes secondary water conduit means for conducting said water to said secondary cartridge means whereby said additional powder or powder concentrate contained within said secondary cartridge means is adapted to be dissolved in said water for producing a secondary concentrate solution therein, secondary withdrawal means including a conduit connected to said secondary cartridge means for withdrawing said secondary concentrate solution from said secondary cartridge means, and secondary mixing means for mixing said secondary concentrate solution with said concentrate solution withdrawn from said recirculation means so as to provide a combined concentrate solution.

6. The apparatus of claim 5 including secondary concentration determination means for measuring the concentration of said secondary concentrate solution.

7. The apparatus of claim 5 including third concentration determination means for measuring the concentration of said combined concentrate solution.

8. The apparatus of claim 5 including secondary concentration determination means for measuring the concentration of said secondary concentrate solution and third concentration determination means for measuring the concentration of said combined concentrate solution.

9. The apparatus of claim 7 or 8 further comprising pump means for controlling the flow of said combined concentrate solution.

10. The apparatus of claim 5 including tertiary cartridge means having additional powder or powder. concentrate therein, and wherein said water supply means includes tertiary water conduit means for conducting said water to said tertiary cartridge means whereby said additional powder or powder concentrate contained within said tertiary cartridge means is adapted to be dissolved in said water for producing a tertiary concentrate solution produced therein, tertiary withdrawal means including a conduit connected to said tertiary cartridge means for withdrawing said tertiary concentrate solution from said tertiary cartridge means, and a tertiary mixing means for mixing said tertiary concentrate solution with at least one of said concentrate solution withdrawn from said recirculation means and said secondary concentrate solution.

11. The apparatus of claim 10 further including final concentration determination means for measuring the concentration of said combined concentrate solution and said tertiary concentrate solution.

12. The apparatus of claim 1 including closure valve means associated with said water supply means whereby said supply of said water can be terminated when said dissolution means contains a predetermined quantity of said water.

13. Apparatus for the preparation of a concentrate solution from water and powder or powder concentrate comprising water supply means for supplying said water, dissolution means for dissolving said powder or powder concentrate in said water, said dissolution means comprising a container whereby said water supply means is adapted to supply said water to said container and at least a portion of said powder or powder concentrate can be dissolved in said water so as to provide said concentrate solution in said container, first withdrawal means for withdrawing said concentrate solution comprising a mixture of said water and said powder or powder concentrate from said container, recirculation means for recirculating said concentrate solution into said container for further dissolution of said water with said powder or powder concentrate, said recirculation means including at least one conduit for providing a recirculation path for said concentrate solution during said recirculation, cartridge means containing powder or powder concentrate connected to said at least one conduit, whereby during said recirculation, said concentrate solution passes through said cartridge means so that said powder or powder concentrate contained within said cartridge means can be dissolved in said recirculating concentrate solution to further concentrate said concentrate solution to a predetermined concentration, said recirculation means further including concentration determination means for determining the concentration of said concentrate solution and regulating the concentration thereof, and valve means connected to said at least one conduit, said valve means being operatively associated with said concentration determination means for selectively providing a flowpath for said concentrate solution recirculating in said at least one conduit to said cartridge means in response to said concentration determination means, second withdrawal means including a conduit for withdrawing said concentrate solution from said recirculation means when said concentrate solution reaches said predetermined concentration, secondary cartridge means containing additional powder or powder concentrate, said water supply means including secondary water conduit means for conducting said water to said secondary cartridge means, whereby said additional powder or powder concentrate contained within said secondary cartridge means can be dissolved in said water and a secondary concentrate solution produced therein, and secondary dissolution means for dissolving said secondary concentrate solution with said concentrate solution withdrawn from said recirculation means by said second withdrawal means so as to provide a combined concentrate solution.

14. The apparatus of claim 13 wherein said concentration determination means includes conductivity measuring means for measuring the conductivity of said concentrate solution.

15. The apparatus of claim 13 including third concentration determination means for measuring the concentration of said combined concentrate solution.

16. The apparatus of claim 13 including secondary concentration determination means for measuring the concentration of said secondary concentrate solution and third conductivity measuring means for measuring the conductivity of said combined concentrate solution.

17. The apparatus of claim 15 or 16 wherein said recirculation means includes pump means connected to said at least one conduit for controlling the flow of said combined concentrate solution.

18. The apparatus of claim 13 including tertiary cartridge means having additional powder or powder concentrate therein, wherein said water supply means includes tertiary water conduit means for conducting said water to said tertiary cartridge means whereby said additional powder or powder concentrate contained within said tertiary cartridge means can be mixed with said water and a tertiary concentrate solution produced therein, tertiary withdrawal means including a conduit for withdrawing tertiary concentrate solution from said tertiary cartridge means, and tertiary mixing means for mixing said tertiary concentrate solution with said at least one of said concentrate solution withdrawn from said recirculation means and said secondary concentrate solution.

19. Apparatus for the preparation of a concentrate solution from water and powder or powder concentrate comprising water supply means for supplying said water, cartridge means for retaining said powder or powder concentrate, dissolution means for dissolving said powder or powder concentrate with said water whereby said water supply means is adapted to supply said water to said cartridge means in order to dissolve at least a portion of said powder or powder concentrate and provide said concentrate solution in said cartridge means, and recirculation means for withdrawing said concentrate solution from said cartridge means and recirculating said concentrate solution through said cartridge means to further concentrate said concentrate solution to a predetermined concentration, said recirculation means including at least one conduit for providing a recirculation path for said concentrate solution during said recirculation, said at least one conduit being connected to said cartridge means so that said concentrate solution flows through said at least one conduit into said cartridge means, concentration determination means arranged in the flowpath defined by said at least one conduit for determining the concentration of said concentrate solution and regulating the concentration thereof until said predetermined concentration is obtained, and valve means connected to said at least one conduit, said valve means being operatively associated with said concentration determination means for selectively providing a flowpath for said concentrate solution to said cartridge means in response to said concentration determination means whereby said powder contained within said cartridge means is further dissolved in said concentrate solution.

20. The apparatus of claim 19, wherein said dissolution means comprises a container.

21. The apparatus of claim 19 including recirculation pump means for facilitating said recirculation of said concentrate solution in said recirculation means.

22. The apparatus of claim 19 wherein said water supply means includes inlet valve means for supplying said water to said recirculation means, and wherein said recirculation means includes outlet valve means for withdrawing said concentrate solution from said recirculation means.

23. The apparatus of claim 22 wherein said concentration determination means includes conductivity measuring means for measuring the conductivity of said concentrate solution in said recirculation means.

24. The apparatus of claim 23 including control means for opening and closing said outlet valve means based upon said measurement of said conductivity measuring means.

25. The apparatus of claim 19 wherein said cartridge means comprises a plurality of cartridge members.

* * * * *

UNITED STATES PATENT AND TRADEMARK OFFICE
CERTIFICATE OF CORRECTION

PATENT NO.  : 5,344,231

DATED       : September 6, 1994

INVENTOR(S) : Jonsson et al.

It is certified that error appears in the above-identified patent and that said Letters Patent is hereby corrected as shown below:

Column 7, line 52, "Kcl" should read --KCl--.
Column 7, line 54, "Cacl" should read --CaCl--.

Signed and Sealed this

Seventh Day of February, 1995

Attest:

BRUCE LEHMAN

Attesting Officer    Commissioner of Patents and Trademarks